(12) United States Patent
Stinson (10) Patent No.: US 7,993,391 B2
(45) Date of Patent: Aug. 9, 2011

(54) MEDICAL DEVICES AND METHODS OF MAKING THE SAME

(75) Inventor: Jonathan S. Stinson, Minneapolis, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 1578 days.

(21) Appl. No.: 11/326,081

(22) Filed: Jan. 5, 2006

(65) Prior Publication Data
US 2006/0116755 A1 Jun. 1, 2006

Related U.S. Application Data

(63) Continuation of application No. 10/229,548, filed on Aug. 28, 2002, now Pat. No. 7,029,495.

(51) Int. Cl.
*A61F 2/06* (2006.01)
(52) U.S. Cl. ...................................... 623/1.44; 623/1.54
(58) Field of Classification Search .................. 623/1.4, 623/1.22, 1.34, 1.38, 1.42–1.49, 1.54; 424/422–425
See application file for complete search history.

(56) References Cited

U.S. PATENT DOCUMENTS

| | | | | |
|---|---|---|---|---|
| 4,332,035 | A | * | 6/1982 | Mano ............................ 623/1.49 |
| 5,024,671 | A | * | 6/1991 | Tu et al. ........................ 623/1.42 |
| 5,195,969 | A | | 3/1993 | Wang et al. |
| 5,270,086 | A | | 12/1993 | Hamlin |
| 5,366,504 | A | | 11/1994 | Andersen et al. |
| 5,605,693 | A | | 2/1997 | Seare |
| 5,629,077 | A | | 5/1997 | Turnlund et al. |
| 5,674,242 | A | | 10/1997 | Phan et al. |
| 5,679,470 | A | | 10/1997 | Mayer |
| 5,709,713 | A | | 1/1998 | Evans et al. |
| 5,718,973 | A | | 2/1998 | Lewis et al. |
| 5,725,570 | A | | 3/1998 | Heath |
| 5,733,326 | A | | 3/1998 | Tomonto et al. |
| 5,780,807 | A | | 7/1998 | Saunders |
| 5,797,877 | A | | 8/1998 | Hamilton et al. |
| 5,843,172 | A | * | 12/1998 | Yan .............................. 623/1.42 |
| 5,980,972 | A | | 11/1999 | Ding |
| 6,015,432 | A | | 1/2000 | Rakos et al. |
| 6,066,100 | A | | 5/2000 | Willard et al. |
| 6,161,399 | A | | 12/2000 | Jayaraman |
| 6,162,244 | A | | 12/2000 | Braun et al. |
| 6,248,129 | B1 | | 6/2001 | Froix |
| 6,312,458 | B1 | | 11/2001 | Golds |
| 6,335,029 | B1 | | 1/2002 | Kamath et al. |
| 6,340,441 | B1 | | 1/2002 | Meyer et al. |
| 6,719,783 | B2 | * | 4/2004 | Lentz et al. ..................... 623/1.4 |
| 6,913,762 | B2 | * | 7/2005 | Caplice et al. ................. 424/423 |
| 2002/0016596 | A1 | | 2/2002 | Cooper | |

FOREIGN PATENT DOCUMENTS

GB 1580691 12/1980
(Continued)

OTHER PUBLICATIONS

Harper, Charles A., "Handbook of Plastics and Elastomers", 1975, 4 pages.
Sheng-Ping et al., U.S. Appl. No. 09/895,415, "Coating a Medical Appliance with a Bubble Jet Printing Head", filed Jul. 2, 2001.
Unknown Japanese Examiner, Office Action, Japanese Application No. 2004-532853 mailed May 26, 2009, 3 pages (English translation).

(Continued)

*Primary Examiner* — Julian W Woo
(74) *Attorney, Agent, or Firm* — Fish & Richardson P.C.

(57) ABSTRACT

Medical devices, for example, implantable devices such as endoprostheses, include a composite material having a polymer.

4 Claims, 7 Drawing Sheets

FOREIGN PATENT DOCUMENTS

| | | |
|---|---|---|
| JP | 2002-104914 | 4/2002 |
| WO | 99/37243 | 7/1999 |
| WO | WO 99/32051 | 7/1999 |
| WO | WO 00/13717 | 3/2000 |
| WO | WO 00/38590 | 7/2000 |

OTHER PUBLICATIONS

Unknown Japanese Examiner, Notice of Rejection in JP Application No. 2004-532853 mailed Mar. 2, 2010, 2 pages.

* cited by examiner

MEDICAL DEVICES AND METHODS OF MAKING THE SAME

CROSS-REFERENCE TO RELATED APPLICATIONS

This application is a continuation application of and claims priority to U.S. application Ser. No. 10/229,548, filed Aug. 28, 2002 now U.S. Pat. No. 7,029,495, the entire contents of which being hereby fully incorporated by reference.

TECHNICAL FIELD

The invention relates to medical devices, such as, for example, endoprostheses, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprosthesis include stents and covered stents, sometimes called "stent-grafts".

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon expandable endoprosthesis. The balloon can be inflated to deform and to fix the expanded endoprosthesis at a predetermined position in contact with the lumen wall. The balloon can then be deflated, and the catheter withdrawn.

In another technique, a self-expandable endoprosthesis is formed of an elastic material that can be reversibly compacted and expanded, e.g., elastically or through a material phase transition. During introduction into the body, the endoprosthesis is restrained in a compacted condition on a catheter. Upon reaching the desired implantation site, the restraint is removed, for example, by retracting a restraining device such as an outer sheath, enabling the endoprosthesis to self-expand by its own internal elastic restoring force.

To support a passageway open, endoprostheses can be made of relatively stiff and strong materials, such as stainless steel or Nitinol (a nickel-titanium alloy), that can resist compression and/or dislocation of the endoprostheses. The physical or mechanical properties of the endoprosthesis materials, however, sometimes do not closely match those properties of the body vessel, which is relatively compliant and resilient. The mismatch in properties, and the presence of the endoprosthesis (a foreign object) in the body, can cause the vessel to become inflamed and/or re-occluded.

SUMMARY

The invention relates to medical devices, such as, for example, endoprostheses, and methods of making the devices. In one aspect, the invention features endoprostheses that have physical and mechanical properties (e.g., resiliency or compliancy) similar to those of a body vessel, thereby reducing the occurrence of inflammation and/or re-occlusion. At the same time, the endoprostheses have good radial and/or hoop strengths, e.g., to maintain the body vessel open and to resist dislodgement after implantation. In some embodiments, the endoprostheses are formed of a composite including a polymer.

In one aspect, the invention features an endoprosthesis having a tubular member including a polymer matrix and a plurality of fibers in the matrix. The fibers have a stiffness greater than the stiffness of the polymer and are substantially oriented in a predetermined direction. In embodiments, the fibers can be oriented substantially circumferentially, longitudinally, and/or radially relative to a longitudinal axis of the tubular member.

Embodiments may include one or more of the following features. The fibers include a metal (such as gold, tantalum, platinum, or tungsten) and/or a polymer. The fibers are dispersed throughout substantially the entire matrix. The fibers are formed on preselected portions of the tubular member. The fibers extend helically around the tubular member. The fibers are formed in a configuration that enhances the radial, hoop, and/or longitudinal strength of the tubular member. The fibers have a first end that is larger than a second end. The fibers are visible by magnetic resonance imaging. The endoprosthesis further includes a magnetopaque material different than the fibers in the matrix.

The tubular member can be formed of a plurality of polymeric layers. The plurality of polymeric layers can include a layer having fibers oriented substantially longitudinally relative to the tubular member, and a layer having fibers oriented substantially radially or circumferentially relative to the tubular member.

The endoprosthesis can further include a drug-releasing layer on the tubular member. The matrix can include a drug.

The endoprosthesis can be in the form of a balloon-expandable stent.

In another aspect, the invention features an endoprosthesis including a tubular member having a polymer, and a first member extending helically around the tubular member. The first member has a stiffness greater than stiffness of the polymer.

Embodiments may include one or more of the following features. The first member includes a metal and/or a polymer. The tubular member includes a plurality of fibers in the polymer that has a stiffness greater than the stiffness of the polymer and is substantially oriented in a predetermined direction. The polymer encapsulates the first member.

In another aspect, the invention features a endoprosthesis having a tubular member having a first layer including a first polymer, and a second layer including a second polymer and a plurality of fibers in the second polymer. The fibers have a stiffness greater than the stiffness of the polymer and are oriented in a predetermined direction.

Embodiments may include one or more of the following features. The first layer further includes a plurality of fibers oriented in a predetermined direction. The pluralities of fibers in the first and second layers are substantially the same. The pluralities of fibers in the first and second layers are oriented in different directions. The pluralities of fibers in the first and second layers are oriented in the same direction. The first and second polymers are the same polymer.

Embodiments may further include one or more of the following advantages. The medical devices are relatively compatible with magnetic resonance imaging (MRI). The devices can be resected, e.g., after implantation. The devices are relatively resistant to fracture.

Other aspects, features, and advantages of the invention will be apparent from the description of the preferred embodiments thereof and from the claims.

DETAILED DESCRIPTION

Figure 1:
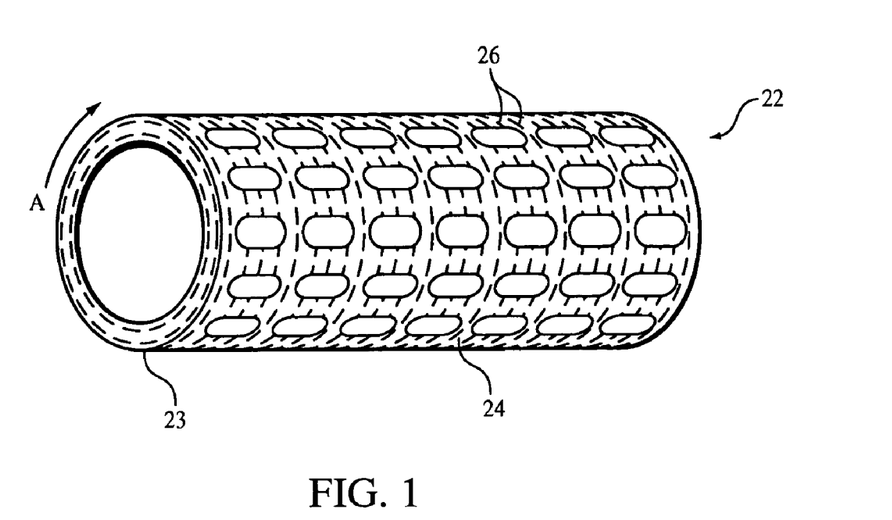
FIG. 1 is an illustration an embodiment of an endoprosthesis.

FIG. 1 shows an endoprosthesis 22, here, a slotted tube stent, including a tubular member 23 formed of a matrix of polymer 24 and a plurality of fibers 26 preferentially oriented in a predetermined direction within the matrix. The polymer provides endoprosthesis 22 with mechanical properties, such as resiliency and compliancy, that match well with the mechanical properties of a body vessel. As a result, the occurrence of inflammation and/or re-occlusion can be reduced. Fibers 26 are formed of a material, such as a metal, that is stiffer than the polymer and can reinforce matrix 24. As shown in FIG. 1, fibers 26 are oriented circumferentially (arrow A) around tubular member 23. As a result, fibers 26 can enhance the hoop strength of tubular member 23, which helps endoprosthesis 22 to resist compression, thereby maintaining the body vessel open.

Other orientations of fibers 26 are possible. In embodiments, fibers 26 are oriented in one or more directions to strengthen matrix 24 (e.g., relative to the matrix with the fibers) along the loading axes of endoprosthesis 22, such as in the radial and/or hoop direction. For example, referring to FIG. 2, an endoprosthesis 42 includes fibers 26 that are oriented radially (arrow B) to enhance the radial strength of the endoprosthesis. Fibers 26 can be oriented longitudinally, i.e., parallel to the length of the endoprosthesis, which can enhance axial stiffness.

Figure 3:
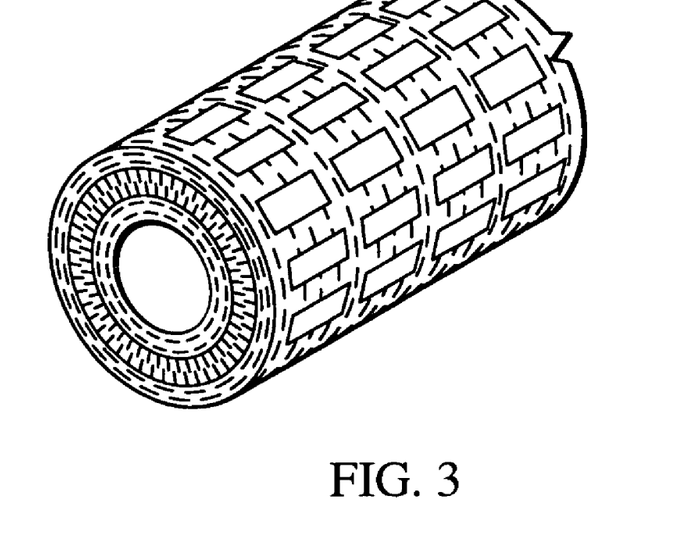
FIG. 3 is an illustration an embodiment of an endoprosthesis.
Figure 4:
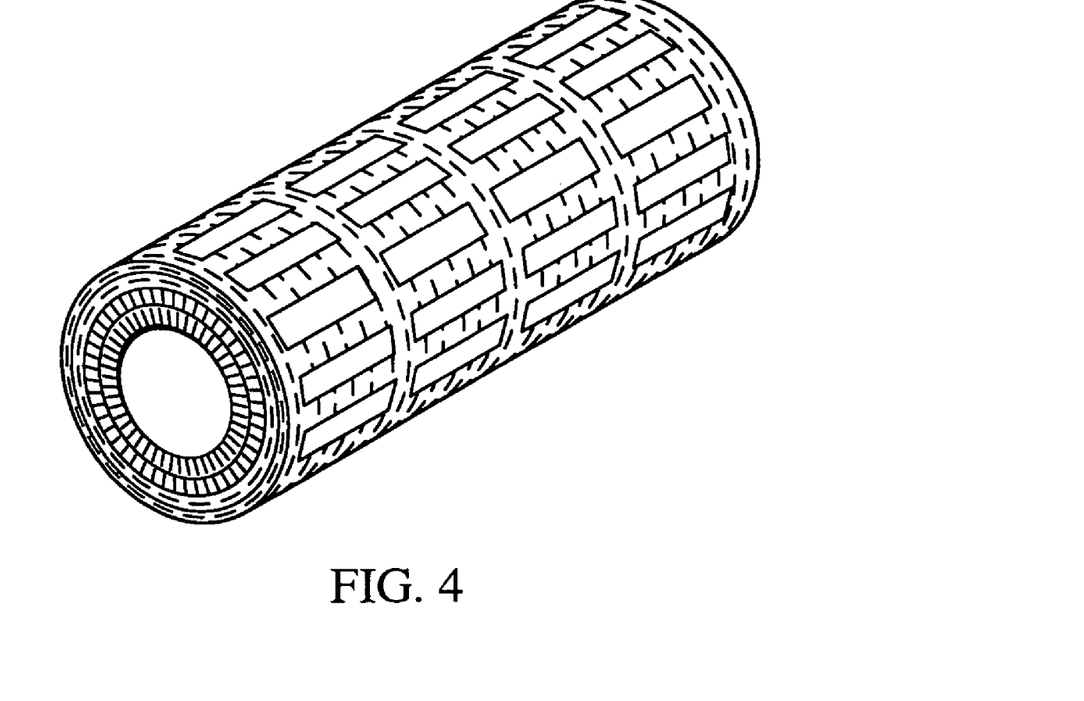
FIG. 4 is an illustration an embodiment of an endoprosthesis.

In some embodiments, an endoprosthesis is formed of multiple layers, e.g., greater than or equal to two, three, four, five or six layers. The layers can be the same or different relative to each other, e.g., with respect to the type and/or composition of polymer(s) and/or fiber, the amount of fiber in each layer, and/or the orientation of the fibers. For example, a multilayer endoprosthesis may include one or more layers having fibers that are oriented radially, one or more layers having fibers that are oriented circumferentially, and/or one or more layers having no fibers, which can enhance the compliancy and resiliency of the endoprosthesis. The layers can have the same or different thickness. Any combination or sequencing of layering is possible, depending on the desired mechanical and physical properties. For example, to provide an endoprosthesis with both good hoop strength and radial strength, an endoprosthesis may include layers of radially oriented fibers alternating with layers of circumferentially oriented fibers (FIG. 3). The layers can be grouped together, e.g., the layers with radially oriented fibers can be the inner layers and the layers with circumferentially oriented fibers can be the outer layers, or vice versa (FIG. 4).

Figure 5:
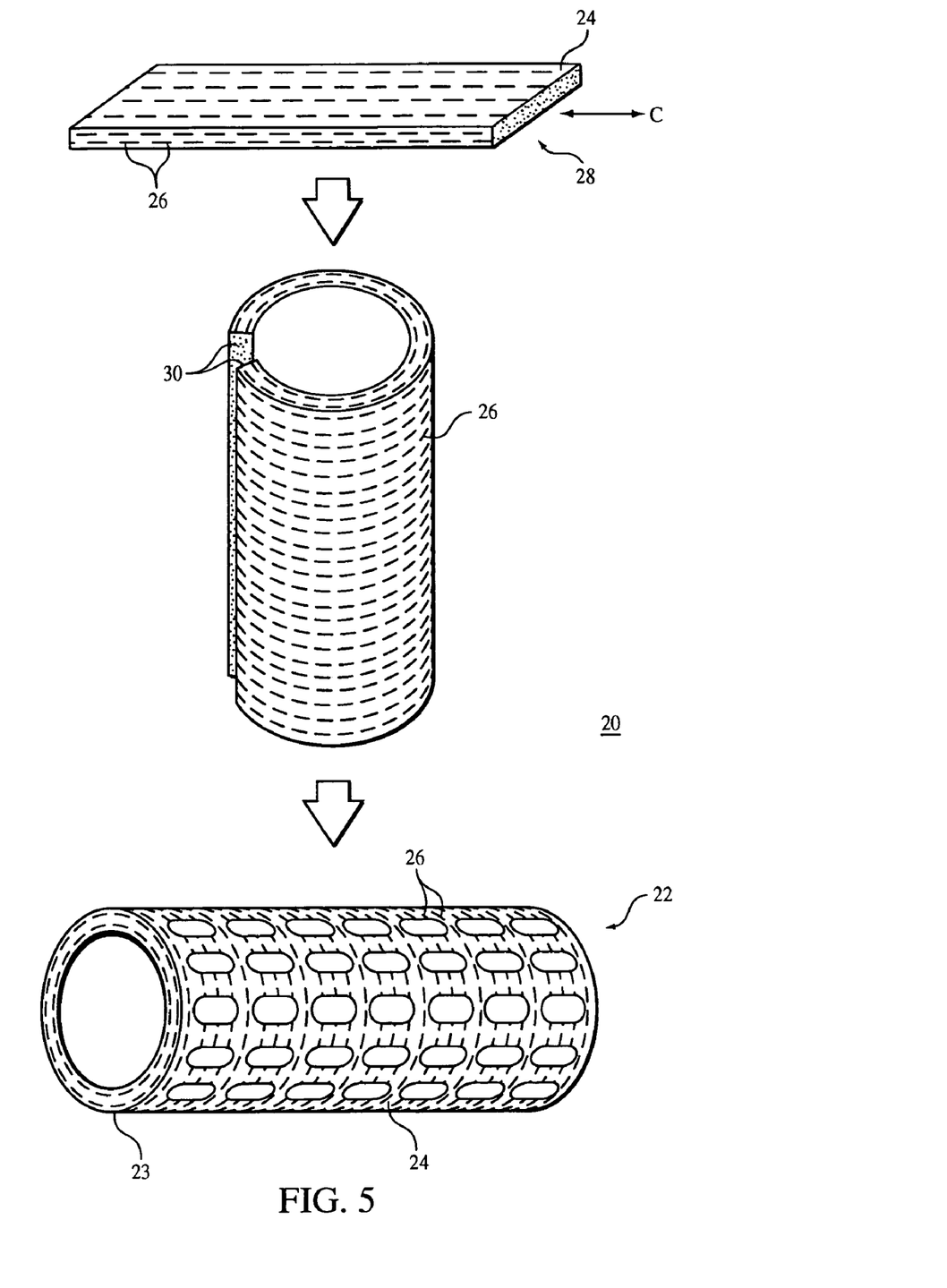
FIG. 5 is an illustration an embodiment of a method of making the endoprosthesis of FIG. 1.

Referring to FIG. 5, a method 20 of making endoprosthesis 22 having circumferentially oriented fibers 26 generally includes forming a polymeric sheet 28 having the fibers oriented parallel to longitudinal axis C of the sheet. Methods of making sheet 28 include, for example, forming a mixture of the polymer of matrix 24 and fibers 26, and pultruding the mixture. Pultrusion is described in, for example, C. A. Harper, Handbook of Plastics and Elastomers, McGraw-Hill Book Co., New York 1975, 5-88 to 5-89, hereby incorporated by reference. In other embodiments, sheet 28 can be formed by positioning, e.g., laying flat, fibers 26 in a desired orientation in a mold. The matrix polymer can then be introduced into the mold in a solid or liquid state. Heat and/or pressure are then applied to allow the polymer to encapsulate the fibers.

Sheet 28 can then be wound, e.g., circumferentially, around a mandrel, and opposing edges 30 of the sheet can be joined together, e.g., by welding or by an adhesive, to form tubular member 23. Tubular member 23 can be drawn and/or cut to size, as needed, and portions of the tubular member are removed to form openings 32 of endoprosthesis 22. Endoprosthesis 22 can be cut and/or formed by laser cutting, as described in U.S. Pat. No. 5,780,807, hereby incorporated by reference in its entirety. In other embodiments, a plurality of sheets 28 can be laminated together, e.g., using an adhesive or by heat bonding, and wrapped around a mandrel to form tubular member 23 and endoprosthesis 22.

Figure 6:
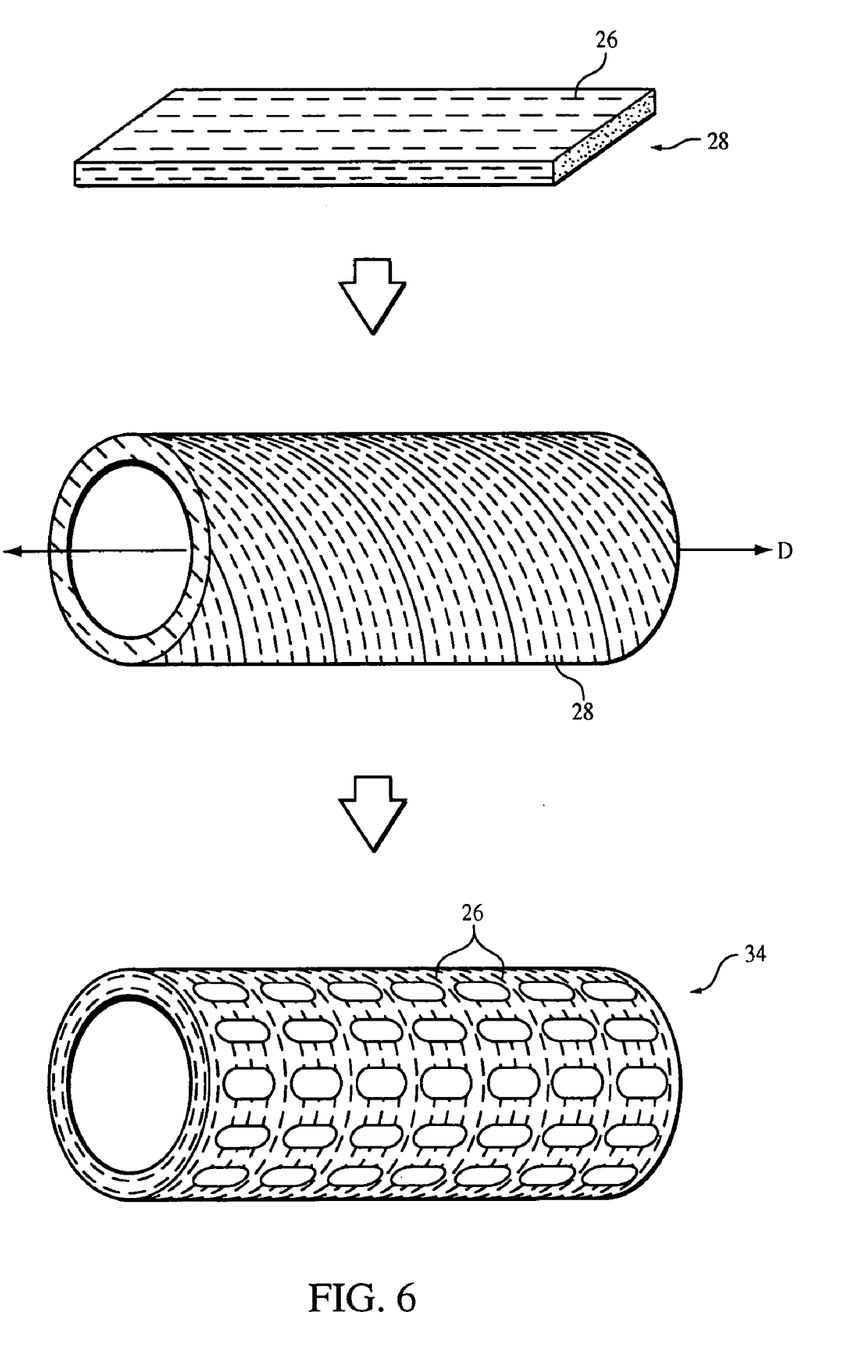
FIG. 6 is an illustration an embodiment of a method of making an endoprosthesis.

In some cases, the orientation of fibers 26 may change from their initial orientation when the endoprosthesis is expanded during use. Referring to FIG. 6, to compensate for a change in the orientation of fibers 26, an endoprosthesis 34 can be formed in which strips of sheet 28 are wound, e.g., helically, at a predetermined initial angle around the mandrel. When endoprosthesis 34 is radially expanded during use, strips 28 and fibers 26 can orient to a desired final orientation, e.g., substantially circumferentially and perpendicular to longitudinal axis D of endoprosthesis 34. The initial winding angle of strips 28 can be, for example, from about 5 to about 85 degrees relative to axis D. Adjacent edges of strips 28 can be joined together, for example, by gluing the edges and/or selectively melting and re-solidifying the edges.

Figure 2:
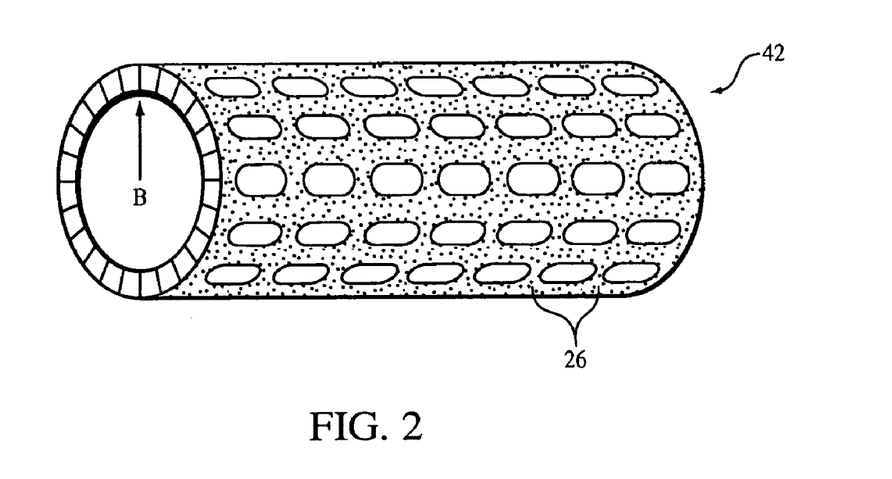
FIG. 2 is an illustration an embodiment of an endoprosthesis.
Figure 7:
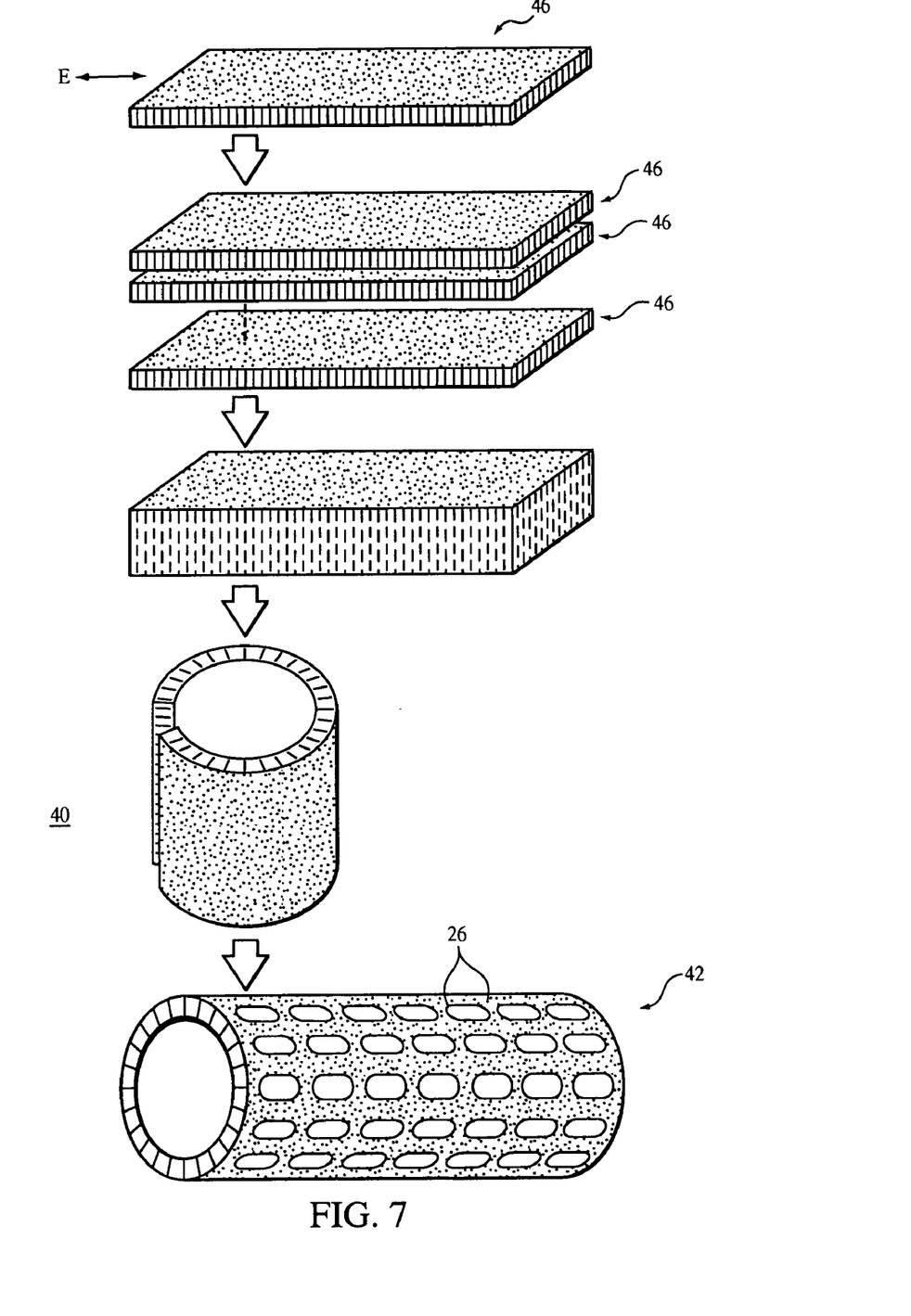
FIG. 7 is an illustration an embodiment of a method of making an endoprosthesis.

Referring to FIGS. 2 and 7, a method 40 of making endoprosthesis 42 having radially oriented fibers 26 includes forming a polymeric sheet 46 in which the fibers are oriented perpendicular to longitudinal axis E of the sheet. After sheet 46 with oriented fibers 44 is formed, the sheet can be formed into endoprosthesis 42 as described above. For example, sheet 46 or strips of the sheet can be wound, e.g., circumferentially or helically, around a mandrel, and edges of the sheet can be bonded together to form a tubular member. The tubular member can then be formed into endoprosthesis 42, e.g., by laser cutting. As shown in FIG. 7, multiple sheets 46 are laminated together, and the multilayer laminate can be wound around the mandrel and formed into endoprosthesis 42.

Numerous methods can be used to orient fibers 26 perpendicular to longitudinal axis E of sheet 46. For example, fibers 26 can be manually pressed into an unsolidified sheet of polymer, and/or the fibers can be sprayed into an unsolidified sheet of polymer using a spray nozzle with an appropriate size and geometry. Fibers 26 can be formed having a first end heavier than a second end, e.g., by forming a stub on the first end or by tapering the size of the fiber. The fibers are then placed into an unsolidified sheet of polymer. The heavier ends of the fibers tend to align the fibers perpendicular to longitudinal axis E of sheet 46. In other embodiments, asymmetrical fibers, e.g., those having one end heavier than another end, can be mixed with the matrix polymer and spin casted (e.g., about the longitudinal axis) in a mold to form a tubular member. The centrifugal force generated during spin casting can orient the fibers in the polymer, e.g., the fibers can orient radially, with the heavier ends outward of the lighter ends.

In some embodiments, magnetic fibers 26, e.g., ferromagnetic or paramagnetic fibers, such as 300 series stainless steel, can be oriented by placing an unsolidified sheet having the fibers in a magnetic field such that the magnetic flux lines are perpendicular to longitudinal axis E of the sheet. To compensate for changes in the orientation of fibers 26 during expansion of endoprosthesis 42, the magnetic flux lines may be non-perpendicular to longitudinal axis E to orient fibers 26 in a desired initial orientation.

A multilayer endoprosthesis in which the layers are different can be made by winding a sheet of polymer (with or without fibers) around a preformed tubular member. For example, to form the endoprosthesis shown in FIG. 3, the innermost layer can be formed by method 20 to form tubular member 23. Sheet 46 can then be wrapped and secured around tubular member 23. A second sheet 28 can then be wound around and secured to sheet 46. In other embodiments, close fitting tubular members (with or without fibers) having an adhesive material between the tubular members can be co-drawn to form a multilayer endoprosthesis.

The polymer used in the endoprostheses described herein can be any polymer that is biocompatible. For example, for vascular stents or stent-grafts, the polymer preferably has acceptable vascular compatibility, e.g., relatively low thrombogenecity and low cytotoxicity. For non-vascular stents or stent-grafts, the polymer is preferably stable in various bodily fluids. The polymer can be biodegradable, for example, if the polymer is used for temporary endoprostheses.

In some embodiments, the polymer can be relatively stiff or hard, e.g., having a hardness of more than about 50 Shore D, such as 72 Shore D or more. In multilayer endoprostheses, the layers may or may not include the same polymer. The difference in hardness of adjacently bonded layers can be about 40 Shore D or less, such as 20 Shore D or less, which can enhance compatibility between the layers, and/or reduce delamination at the interface. Hardness may be measured according to ASTM D2240.

In embodiments, the polymer can have an elastic modulus of about 10,000-2,000,000 psi. The elastic modulus can be equal to or greater than about 100,000, 500,000, 1,000,000, or 1,500,000 psi; and/or equal to or less than 2,000,000, 1,500, 000, 1,000,000, 500,000, or 100,000 psi. Alternatively or in addition, the polymer can have an elongation to fracture equal to or greater than about 10%, e.g., equal to or greater than about 20%, 30%, 40%, or 50%. Alternatively or in addition, the polymer can have a yield strength equal to or greater than about 10,000 psi, e.g., equal to or greater than about 25,000 psi or 50,000 psi.

The polymer may be of a substantially pure polymer or may be blends of different polymers. The polymer can be made of block copolymers including common block moieties, which can enhance compatibility, while maintaining defect retardation. For example, the block moieties may be amide segments and tetramethylene glycol segments. An example is the PEBAX® family of polymers, which can be used pure or as blends (available from Atofina, Philadelphia, Pa.). For example, PEBAX® 5533 (55 Shore D) can be blended with PEBAX® 2533 (25 Shore D) in a weight ratio of about 4 to 1 to provide a soft polymer of about 50 Shore D. Another combination of polymers is polybutylene terephthalate (PBT) such as CELANEX® (over 80 Shore D, from Ticona, Summit, N.J.) and polyester/ether block copolymer available as ARNITEL® (55 Shore D, from DSM, Erionspilla, Ind.). Another combination of polymers is PBT and one or more PBT thermoplastic elastomers, such as RITEFLEX® (55 Shore D from Ticona in Summit, N.J.) and HYTREL® (55 Shore D from E. I. Dupont de Nemours, Wilmington, Del.) for example. Still another combination of polymers is polyethylene terephthalate (PET) and a thermoplastic elastomer, such as a PBT thermoplastic elastomer (e.g., ARNITEL®, HYTREL®, or RITEFLEX®).

In certain embodiments, one or more layers can contain one or more nylons. For example, a combination of polymers is a nylon and a PEBAX®-type material, such as PEBAX®, GRILON®, GRILAMID® (EMS) and/or VESTAMID® (Creanova). Examples of nylons include aliphatic nylons, such as Nylon 11 (Elf Atochem), Nylon 6 (Allied Signal), Nylon 6/10 (BASF), Nylon 6/12 (Ashley Polymers) and Nylon 12. Additional examples of nylons include aromatic nylons, such as GRIVORY® (EMS) and Nylon MXD-6. Other nylons and/or combinations of nylons can be used.

In some embodiments, one or more layers can contain a liquid crystal polymer (LCP) (e.g., a composite material having the LCP incorporated therein). Examples of LCPs include polyester(s), polyamide(s) and/or their copolymers, such as VECTRA® A (Ticona), VECTRA® B (Ticona) and VECTRA® LKX (Ticona) (e.g., VECTRA® LKX 1111 (Ticona)). Other LCPs and/or combinations of LCPs can be used.

The LCP can be incorporated into one or more polymers, such as, for example, a PEBAX®-type material, a nylon, a thermoplastic polyester and/or thermoplastic elastomer versions thereof. In certain embodiments, the liquid crystal polymer can be incorporated into one or more of the polymer layers to form a hard layer of material (e.g., a layer of material with more than about 60 Shore D hardness, such as more than about 65 Shore D hardness). In one combination, an LCP is incorporated into a layer containing one or more PEBAX®-type materials, such as PEBAX®, GRILON®, GRILAMID®, and/or VESTAMID®. In certain embodiments, an LCP-containing composition can be relatively stiff in the direction of melt flow. Without wishing to be bound by theory, it is believed that this may result because LCP crystals (e.g., fibers) form or align in the melt flow direction as the polymer composite cools from a liquid state to a solid state. It is believed that the LCP fibers can reinforce the other polymer(s) contained in the layer (e.g., matrix polymer(s)).

The amount of LCP contained in the tube or balloon can vary depending upon its intended use. In some embodiments, as the percentage of LCP in a composite material is decreased, the individual layer thickness and the overall thickness of one or more layers of an LCP-containing composite material can be increased.

The LCP content of a tube can be at least about 0.1 weight percent, such as from about 0.1 weight percent to about 20 weight percent (e.g., from about 0.5 weight percent to about 10 weight percent, from about one to about five weight percent). Within a given layer, the LCP content can be at least about 0.1 weight percent (e.g., from about one weight percent to about 50 weight percent, from about five weight percent to about 20 weight percent, from about five weight percent to about 15 weight percent).

In certain multilayer endoprostheses, an adhesion enhancing material can be incorporated into one or more material layers. An adhesion enhancing material can be used, for example, to enhance the adhesion between adjacent layers. Examples of adhesion enhancing materials include epoxy or anhydride modified polyolefins, such as LOTADER® (Elf Atochem) and KODAR® PETG (Eastman Kodak). An adhesion enhancing material can be added to a material (e.g., a composition containing one or more polymers), e.g., prior to molding or pultrusion. For example, in embodiments in which alternate layers include PET and PBT, PETG can be added to the PET.

The amount of adhesion enhancing material can vary depending upon the intended use. In some embodiments, a sufficient amount of adhesion enhancing material(s) are included in the material so that the adhesion enhancing material(s) makes up at least about 0.5 percent of the resulting mixture that forms the layer (e.g., at least about one percent, at least about five percent, at least about 10 percent) and/or at most about 20 percent of the resulting mixture that forms the layer (e.g., at most about 15 percent, at most about 12 percent, at most about 10 percent).

In some embodiments, a compatibilizing material can be incorporated into one or more material layers. The compatibilizing material can be designed, for example, to modify one or more phase boundaries of the LCP(s) and one or more of the other polymer(s) (e.g., thermoplastic polymer(s)) and/or to enhance adhesion between the LCPs and one or more of the other polymer(s). The compatibilizing material can be a copolymer, such as a block copolymer, including moieties of at least two different chemical structures, respectively providing compatibility with an LCP and one or more other polymers in the mixture. The compatibilizing material can be a reactive polymer that reacts with the LCP and/or one or more other polymers in the mixture. The compatibilizing material can be a catalyst that promotes a reaction between the LCP and one or more other polymers in the mixture. Other compatibilizing materials can be used. Combinations of compatibilizing materials can be used.

Examples of compatibilizing materials include copolyester elastomers, ethylene unsaturated ester copolymers, such as ethylene-maleic anhydride copolymers, copolymers of ethylene and a carboxylic acid or acid derivative, such as ethylene-methyl acrylate copolymers, polyolefins or ethylene-unsaturated ester copolymers grafted with functional monomers, such as ethylene-methyl acrylate copolymers, copolymers of ethylene and a carboxylic acid or acid derivative, such as ethylene-methyl acrylate maleic anhydride terpolymers, terpolymers of ethylene, unsaturated ester and a carboxylic acid or acid derivative, such as ethylene-methyl acrylate-methacrylic acid terpolymers, maleic acid grafted styrene-ethylene-butadiene-styrene block copolymers, and acrylic acid elastomers, such as acrylic rubbers. Similar polymers containing epoxy functional groups, for instance derived from glycidyl methylacrylate (e.g., alkyl(meth)acrylate-ethylene-glycidyl (meth)acrylate polymers) can be used. Ionomeric copolymers can be used. PETG can be used. Examples of compatibilizing materials include HYTREL® HTR-6108, POLYBOND® 3009 (BP Chemicals), SP 2205 (Chevron), DS 1328/60 (Chevron), LOTADER® 2400, ESCOR® ATX-320, ESCOR® ATX-325, VAMAC® G1 and LOTADER® AX8660. In certain embodiments, a compatibilizing material (e.g., PETG) can be mixed with one or more polymers (e.g., an LCP-containing material), e.g., prior to extrusion.

There are many ways in which LCPs can be blended into thermoplastics. The LCP blend can be a ternary system of LCP, thermoplastic and compatibilizing materials. Systems with multiple combinations of different LCPs, different thermoplastics and different compatibilizing materials are contemplated.

The compatibilized blend can be a blend of polyazomethine LCP, a thermoplastic polymer such as a polyamide, and a compatibilizing material such as a caprolactum having at least one functional group capable of showing compatibility and/or reactivity to the LCP and/or the thermoplastic polymer. Such blends are described, for example, in U.S. Pat. No. 5,565,530, which is hereby incorporated by reference.

One polymer blend product which can be used include PET, a wholly aromatic LCP copolyester and an ethylene-methyl acrylate-acrylic acid terpolymer compatibilizing material, such as, for example, ESCOR® ATX320, ESCOR® ATX325, or ESCOR® XV-11.04. Another polymer blend product includes PET, a wholly aromatic LCP copolyester and an ethylene-maleic anhydride copolymer compatibilizing material, such as POLYBOND® 3009. Another polymer blend product includes PET, a wholly aromatic LCP copolyester and an ethylene-methyl acrylate copolymer grated with maleic anhydride compatibilizing material, such as DS 1328/60, or a copolyester elastomer, such as HYTREL® HTR 6108.

Polymer blend products including PET, LCP and at least two compatibilizing materials can be used. For example, DS 1328/60 and POLYBOND® 3009 can be used with the LCP VECTRA®. As an additional example, when the LCP is VECTRA®, the compatibilizing materials can be POLYBOND® 3009 and at least one additional compatibilizing material selected from ESCOR® ATX-320, ESCOR® ATX-325, DS 1328160, ESCOR® XV-11.04 and HYTREL® HTR-6108.

In certain embodiments, consideration is given to the properties of the LCP and the other polymer(s) (e.g., PET), as well as the desired properties of the resulting blend, when selecting the compatibilizing material(s).

In some embodiments containing an LCP, a thermoplastic polymer and compatibilizing material(s), the blend product includes from about 0.1 weight percent to about 10 weight percent (e.g., from about 0.5 weight percent to about 2 percent) LCP, from about 40 weight percent to about 99 weight percent (e.g., from about 85 weight percent to about 99 weight percent) thermoplastic polymer, and from about 0.1 weight percent to about 30 weight percent (e.g., from about one weight percent to about 10 weight percent) compatibilizing material(s).

While certain polymers and polymer combinations are discussed above, other polymers and polymer combinations can also be used. Other polymers include, for example, elastomers such as thermoplastic elastomers and engineering thermoplastic elastomers, such as polybutylene terephthalate-polyethene glycol block copolymers, which are available, for example, as HYTREL®. These are discussed in Hamilton U.S. Pat. No. 5,797,877, the entire content of which is incorporated herein by reference. Other polymers include polyurethenes, polytetrafluoroethylene (PTFE), polylactic acid (PLA), styrene-isobutylene-styrene (SIBS), polypropylene, and polyglycolide. Other polymers include copolymers such as ABS (acrylonitrile-butadiene-styrene), ABS/nylon, ABS/-polyvinyl chloride (PVC), ABS/polycarbonate, acrylonitrile copolymer, polyacrylamide, polyacrylate and polyacrylsulfone, polyesters such as polyethylene terephthalate (PET), polybutylene terephthalate (PBT), polyethylene naphthalate (PEN), liquid crystal polymer (LCP), polyester/polycaprolactone and polyester/polyadipate; and high melt temperature polyethers including polyetheretherketone (PEEK), polyethersulfone (PES), polyetherimide (PEI) and polyetherketone (PEK), polymenthylpentene, polyphenylene ether, polyphenylene sulfide, and styrene acrylonitrile (SAN), polyamides such as nylon 6, nylon 6/6, nylon 6/66, nylon 6/9, nylon 6/10, nylon 6/12, nylon 11, nylon 12, ethylene, propylene ethylene vinylacetate and ethylene vinyl alcohol (EVA), various ionomers, polyethylene type I-IV, polyolefins, polyurethane, polyvinyl chloride, and polysiloxanes (silicones). Those with low to medium melt temperatures include fluorocarbons such as polychlorotriethylene (CTFE), poly[ethylene-co-chlorotrifluoroethylene] (ECTFE) copolymer ethylene tetrafluoroethylene (ETFE), copolymer tetrafluoroethylene and hexafluoropropylene (FEP), perfluoroalkane (PFA) and poly[vinylidene fluoride] (PVDF).

In some embodiments, a matrix of polymer includes at least 20 percent by weight of one or more polymers. For example, a matrix can include greater than or equal to 30, 40, 50, 60, 70, 80, or 90 percent by weight of polymer(s); and/or less than or equal to 90, 80, 70, 60, 50, 40, or 30 percent by weight of polymer(s).

Fibers 26 are generally elongated structures having a small circumference or width in proportion to a length or height. Fibers 26 can have a variety of configurations or shapes. Fibers 26 can have a cross section that is substantially circular or substantially non-circular, such as oval, or regularly or irregularly polygonal having 3, 4, 5, 6, 7, or 8 or more sides. The outer surface of fibers 26 can be relatively smooth, e.g., cylindrical or rod-like, or faceted. Fibers 26 can have a surface that is rough and irregular. Fibers 26 can have uniform or non-uniform thickness, e.g., the fibers can taper along their lengths. Mixtures of fibers having two or more different configurations or shapes can be used. A fiber can extend generally linearly or crookedly. Examples of a fiber include a thread, a filament, and a whisker.

Fibers 26 can have a length of about 0.01 mm to about 60 mm. In some embodiments, fibers 26 can have a length greater than or equal to about 1, 10, 20, 30, 40, or 50 mm; and/or less than or equal to about 60, 50, 40, 30, 20, 10, or 1 mm. The lengths of fibers 26 may be uniform or relatively random. Fiber 26 can be a width of about 0.001 to 1 mm. Fibers 26 can have a width greater than or equal to about 0.01, 0.1, 0.5 mm; and/or less than or equal to about 1, 0.5, 0.1, or 0.01 mm. The width can be uniform or relatively random.

In some embodiments, fibers 26 have length to width aspect ratios from about 10:1 to about 6000:1, although higher aspect ratios are possible. In some embodiments, the length to width aspect ratios can be greater than or equal to about 100:1, 500:1, 1000:1, 2500:1, or 5000:1; and/or less than or equal to about 5000:1, 2500:1, 1000:1, 500:1, or 100:1. The lengths and widths are average lengths and average widths, respectively. Mixtures of fibers having two or more different aspect ratios and/or dimensions can be used.

Fibers 26 can be formed of any material that is stiffer and/or stronger, e.g., in the long axis, than the polymer(s) in the matrix of an endoprosthesis. The fiber material can be natural or synthetic. For example, the fiber material can include carbon, ceramics (e.g., oxides, carbides, or nitrides), a metal, an alloy, bone, polysaccharides (e.g., chitosan), cellulose-based fibers, glass fibers (e.g., fiberglass), and/or sutures. The fiber material can include one or more of the polymers described above, e.g., those polymers that have greater stiffness than the stiffness of a selected matrix polymer.

The fiber material can be radiopaque or magnetopaque (i.e., visible by magnetic resonance imaging (MRI)). The fiber material can have low magnetic susceptibility to reduce MRI artifacts. Suitable materials for radiopacity include, for example, gold, platinum, iridium, cobalt, titanium, tungsten, tantalum, stainless steel, Nitinol, and metal alloys containing a sufficient percentage of heavy elements. Suitable materials with low magnetic susceptibility include, for example, non-ferrous metal-alloys containing paramagnetic or diamagnetic elements (e.g., gold, platinum, copper, iridium, titanium, and tantalum). Suitable materials with relatively high magnetic susceptibility include iron, nickel, and cobalt. Mixtures of fibers having two or more different compositions can be used.

The concentration and orientation of the fibers are selected to provide the endoprosthesis with mechanical properties that match well with the mechanical properties of a body vessel while allowing the endoprosthesis to maintain the vessel open. For example, a tubular member and/or a layer that makes up a tubular member can have at least about five percent of fibers by weight. In embodiments, the tubular member and/or layer include greater than or equal to about 5, 10, 15, 20, 25, 30, 35, 40, 45, 50, 60, 70, or 80 weight percent of fibers, and/or less than or equal to about 80, 70, 60, 50, 45, 40, 35, 30, 25, 20, 15, or 10 weight percent of fibers. Multilayer endoprostheses can include layers having the same concentration or different concentrations of fibers.

In some embodiments, the endoprostheses formed by the methods described herein have an elastic modulus along an axis substantially parallel to the reinforcement of about 700,000 psi to about 30,000,000 psi. In other embodiments, the endoprostheses have a modulus of about 1,000,000 psi to about 10,000,000 psi. Yield strength in the direction of reinforcement can be equal to or greater than about 15,000 psi. In embodiments, the endoprostheses can be radially expanded from about 2 mm (O.D.) to about 4 mm (O.D.) without substantial fracture.

In general, the endoprostheses can be of any desired shape and size (e.g., coronary stents, aortic stents, peripheral stents, gastrointestinal stents, urology stents and neurology stents). In certain embodiments, a coronary stent can have an expanded diameter of from about 2 millimeters to about 6 millimeters. In some embodiments, a peripheral stent can have an expanded diameter of from about 5 millimeters to about 24 millimeters. In certain embodiments, a gastrointestinal and/or urology stent can have an expanded diameter of from about 6 millimeters to about 30 millimeters. In some embodiments, a neurology stent can have an expanded diameter of from about 1 millimeter to about 12 millimeters. The endoprostheses can be balloon-expandable, self-expandable, or a combination of both (e.g., U.S. Pat. No. 5,366,504).

In other embodiments, the endoprosthesis can include and/or be attached to a biocompatible, non-porous or semi-porous polymer matrix made of polytetrafluoroethylene (PTFE), expanded PTFE, polyethylene, urethane, or polypropylene. The endoprosthesis can include a releasable therapeutic agent or a pharmaceutically active compound, such as described in U.S. Pat. No. 5,674,242, and commonly-assigned U.S. Ser. No. 09/895,415, filed Jul. 2, 2001. The therapeutic agents or pharmaceutically active compounds can include, for example, anti-thrombogenic agents, antioxidants, anti-inflammatory agents, anesthetic agents, anti-coagulants, and antibiotics.

The endoprosthesis can be used, e.g., delivered and expanded, according to conventional methods. Suitable catheter systems are described in, for example, Wang U.S. Pat. No. 5,195,969, and Hamlin U.S. Pat. No. 5,270,086. Suitable stents and stent delivery are also exemplified by the NIR on Ranger® system, available from Boston Scientific Scimed, Maple Grove, Minn.

OTHER EMBODIMENTS

In embodiments, the fibers are relatively long and continuous. For example, the fibers can continuously extend the entire circumference of a tubular member or an endoprosthesis.

Figure 8:
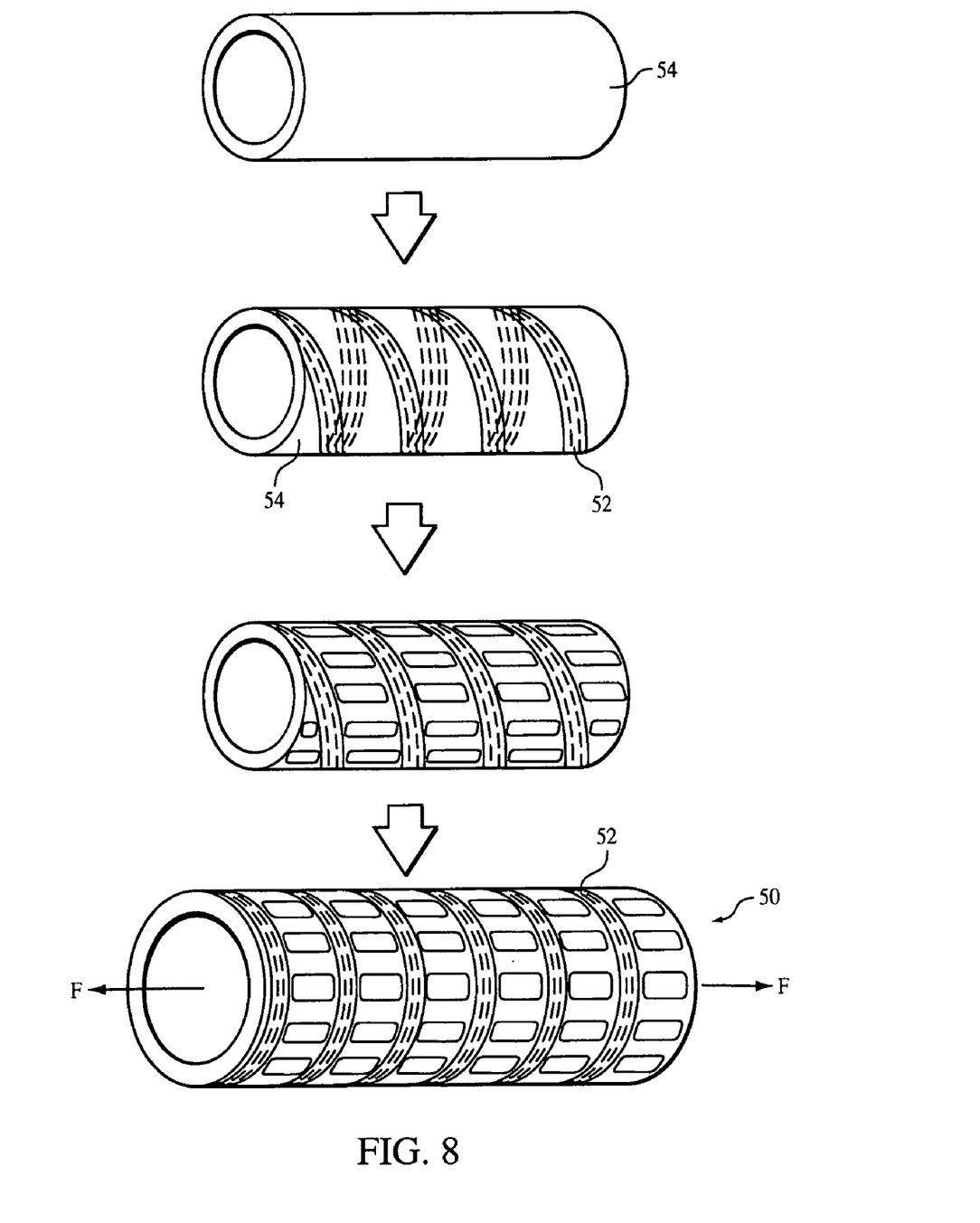
FIG. 8 is an illustration an embodiment of a method of making an endoprosthesis.

In other embodiments, the fibers may be formed on selected portions of the endoprosthesis, e.g., the fibers need not be dispersed throughout the entire endoprosthesis. Referring to FIG. 8, an endoprosthesis 50 includes a polymeric strip 52 that is spaced and helically wound about longitudinal axis F of the endoprosthesis. Strip 52 includes fibers 26 that are oriented, e.g., parallel to or perpendicular to the length of the strip, to provide endoprosthesis 50 with radial and/or hoop strength. Strip 52 can be formed according to methods described above, e.g., for sheet 28 or 46.

To form endoprosthesis 50, strip 52 is wound continuously around and attached to a tubular member 54, e.g., an extruded polymer tube. Strip 52 can be attached, for example, by heat bonding or by using an adhesive. Tubular member 54, which can be made of one or more layers, can be made of a polymer similar to that in polymeric strip 52 or a different polymer. The angle at which strip 52 is wound is selected to provide a desired final orientation of the strip, allowing for any changes in orientation during expansion, if desired. After strip 52 is attached to tubular member 54, endoprosthesis 50 is formed, e.g., by laser cutting.

Other embodiments are contemplated. In some embodiments, one or more additional polymeric layers can be formed over strip 52. The additional layer(s) can be strips wound around strip 52, a tubular member slid over strip 52, and/or a casted or molded member formed over strip 52. The additional layer(s) and/or tubular member 54 may include oriented fibers, e.g., as in endoprosthesis 22 and/or 42. Multiple strips 52 can be used. For example, multiple strips 52 can overlap each other and/or be staggered relative to each other. The strips can be wound as multiple, unconnected bands around tubular member 54. The strips can have fibers that are oriented in the same or different manner. In some cases, no tubular member 54 is used, e.g., strip 52 can be wrapped around a mandrel, and additional layer(s) can be formed over the strip.

Figure 9:
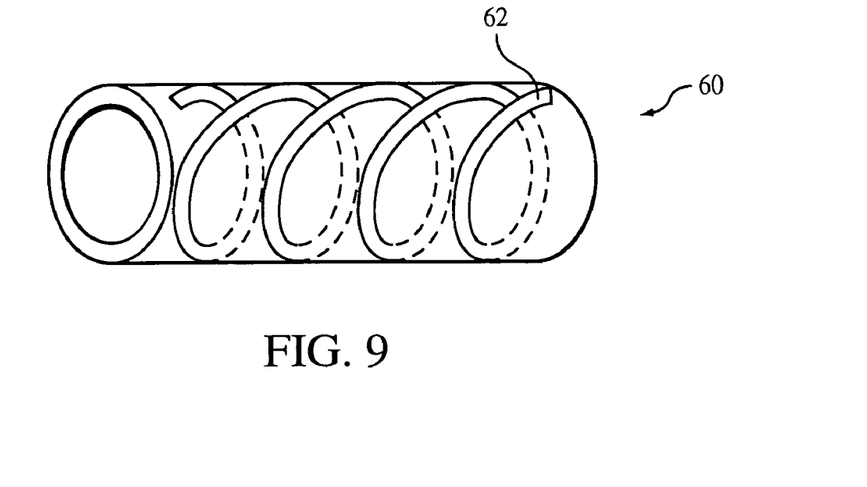
FIG. 9 is an illustration of an embodiment of a tubular member.

Strips 52 can be formed of a non-polymeric material. Referring to FIG. 9, a polymeric tubular member 60 includes a strip 62 in the form of a ribbon wound around the tubular member. A polymeric strip (with or without fibers) can be wound to fill in gaps between strip 62. Strip 62 can be closely wound, e.g., such that the windings are not spaced from each other. Strip 62 can be made of a metal or an alloy, as described above. Strip 62 can be radiopaque or magnetopaque. In other embodiments, strip 62 can be a filament, a wire, or a cable. Tubular member 64 can be generally the same as tubular member 54, described above.

Tubular member 60 can be made into an endoprosthesis by the method shown in FIG. 8. Alternatively, strip 62 can be pre-formed, e.g., pre-wound, and placed into a mold, and a polymer or a mixture of polymers can be introduced into the mold to encapsulate the strip.

Figure 10:
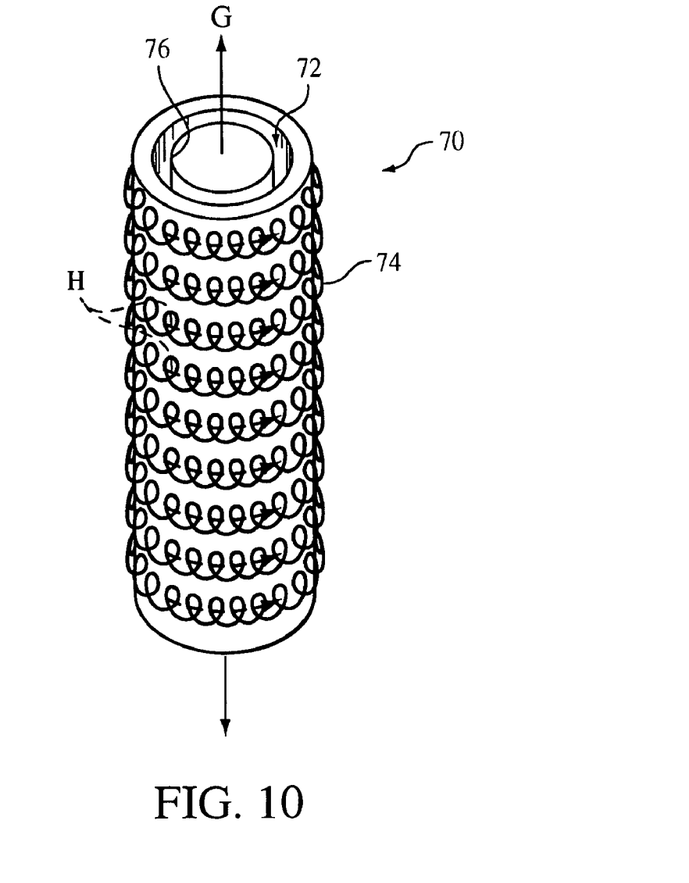
FIG. 10 is an illustration of an embodiment of a device for making an endoprosthesis.

Combinations of methods of making an endoprosthesis can be used. For example, spin casting and magnetic orientation of fibers can be combined to form an endoprosthesis. FIG. 10 shows a tube mold 70 having a tubular cavity 72. Mold 70 is configured to be rotatable around its longitudinal axis G. A coil 74, formed of a pre-wound electrically conducting wire, is wrapped around mold 70. Alternatively or in addition, a second coil is wrapped adjacent to the inner surface 76 of cavity 72. Coil 74 is capable of carrying a current such that a magnetic flux is induced wherein the flux lines extend within the windings of the coil and circumferentially around mold 70 (arrows H). Mold 70 can be made or a diamagnetic material or a paramagnetic material so that the mold does not become magnetic and attract fibers. Mold 70 can be made of, for example, copper, tantalum, or titanium.

During fabrication, a mixture of polymer(s) and fibers, e.g., ferromagnetic or paramagnetic fibers, is introduced to cavity 72. To orient the fibers circumferentially within cavity 72, a current is passed through coil 74 to induce flux lines extending circumferentially about mold 70. As a result, the fibers can circumferentially orient with the induced magnetic field. Mold 70 can be rotated about axis G to enhance uniformity and orientation. In embodiments, no magnetic field is created, but mold 70 is rotated to radially orient the fibers, e.g., asymmetrical fibers, as in spin casting described above.

The subject matter described herein can be applied to other medical devices, such as, for example, catheters, medical tubing, introducer sheaths, and guide wire tips. Examples of balloon catheters are described in, for example, U.S. Pat. No. 5,195,969, and U.S. Pat. No. 5,270,086, all hereby incorporated by reference; and are exemplified by the Ranger® system available from Boston Scientific Scimed, Maple Grove, Minn. Introducer sheaths are described in U.S. Pat. No. 6,066,100, and guide wires are described in U.S. Pat. No. 6,340,441.

All publications, applications, and patents referred to herein are incorporated by reference in their entirety.

Other embodiments are within the claims.

What is claimed is:

1. An endoprosthesis, comprising:
a tubular member having
a first layer including a first polymer matrix encapsulating a plurality of fibers in the first polymer matrix, the fibers having a stiffness greater than stiffness of the first polymer matrix and having lengths in the range of about 0.01 to about 10 millimeters, and being oriented in a first predetermined direction, the first polymer matrix being stable in body fluids; and
a second layer including a second polymer matrix encapsulating a plurality of fibers in the second polymer matrix, the fibers having a stiffness greater than the stiffness of the second polymer matrix, having lengths in the range of about 0.01 to about 10 millimeters, and being oriented in a second predetermined direction, the second predetermined direction being different than the first predetermined direction, the second polymer matrix being stable in body fluids.

2. The endoprosthesis of claim 1, wherein the first and second polymer matrixes comprise the same polymer.

3. The endoprosthesis of claim 1, wherein fibers in both the first polymer matrix and the second polymer matrix have lengths in the range of about 1 to about 10 millimeters.

4. The endoprosthesis of claim 1, wherein fibers in both the first polymer matrix and the second polymer matrix have lengths in the range of about 1 to about 5 millimeters.

* * * * *